(12) United States Patent
Van Damme et al.

(10) Patent No.: US 11,427,815 B2
(45) Date of Patent: Aug. 30, 2022

(54) NUCLEIC ACID PURIFICATION SYSTEM USING A SINGLE WASH AND ELUTION BUFFER SOLUTION

(71) Applicant: KONINKLIJKE PHILIPS N.V., Eindhoven (NL)

(72) Inventors: Hendrik Sibolt Van Damme, 's-Hertogenbosch (NL); Wilbert Hendrik Bouwman, Elst (NL)

(73) Assignee: Koninklijke Philips N.V., Eindhoven (NL)

( * ) Notice: Subject to any disclaimer, the term of this patent is extended or adjusted under 35 U.S.C. 154(b) by 38 days.

(21) Appl. No.: 16/065,843

(22) PCT Filed: Dec. 27, 2016

(86) PCT No.: PCT/EP2016/082733
§ 371 (c)(1),
(2) Date: Jun. 25, 2018

(87) PCT Pub. No.: WO2017/114844
PCT Pub. Date: Jul. 6, 2017

(65) Prior Publication Data
US 2019/0300873 A1 Oct. 3, 2019

(30) Foreign Application Priority Data
Dec. 28, 2015 (EP) .................................... 15202803

(51) Int. Cl.
*C07H 21/00* (2006.01)
*C12N 15/10* (2006.01)
*C12Q 1/6806* (2018.01)

(52) U.S. Cl.
CPC ....... *C12N 15/1006* (2013.01); *C12Q 1/6806* (2013.01)

(58) Field of Classification Search
CPC ................................................ C12N 15/1006
See application file for complete search history.

(56) References Cited

U.S. PATENT DOCUMENTS

| | | | | |
|---|---|---|---|---|
| 4,843,155 | A * | 6/1989 | Chomczynski | .... C12N 15/1003 536/25.41 |
| 5,346,994 | A * | 9/1994 | Chomczynski | .......... C07K 1/14 530/419 |
| 5,945,515 | A * | 8/1999 | Chomczynski | .... C12N 15/1003 530/412 |
| 6,111,096 | A | 8/2000 | Laugharn | |
| 6,274,726 | B1 * | 8/2001 | Laugharn, Jr. | ........ B01L 3/5027 203/1 |
| 8,415,467 | B2 * | 4/2013 | Wu | .................... C08G 73/0206 536/25.4 |
| 8,470,586 | B2 | 6/2013 | Wu et al. | |
| 8,722,329 | B2 | 5/2014 | Young | |
| 9,012,208 | B2 * | 4/2015 | Selden | ............... C12N 15/1003 435/287.2 |
| 9,169,479 | B2 * | 10/2015 | Young | .................. C12Q 1/6806 |
| 9,174,210 | B2 * | 11/2015 | Selden | ...................... B01L 7/52 |
| 9,340,828 | B2 * | 5/2016 | Estmer Nilsson | . C12N 15/1006 |
| 9,422,543 | B2 * | 8/2016 | Chua | .................. C12N 15/1006 |
| 9,455,053 | B2 | 9/2016 | Peng | |
| 9,510,347 | B2 | 11/2016 | Thubert | |
| 9,663,779 | B2 * | 5/2017 | Fabis | ..................... C12N 15/101 |
| 9,883,507 | B2 * | 1/2018 | Thubert | ................ H04W 40/22 |
| 10,062,458 | B2 * | 8/2018 | Xu | ........................ C04B 37/021 |
| 10,464,065 | B2 * | 11/2019 | Selden | ............. B01L 3/502715 |
| 2010/0285578 | A1 | 11/2010 | Selden | |
| 2011/0144286 | A1 | 6/2011 | Wu | |
| 2011/0257386 | A1 | 10/2011 | Chua | |
| 2012/0245337 | A1 | 9/2012 | Fabis | |
| 2013/0122496 | A1 | 5/2013 | Haydock | |
| 2014/0272999 | A1 * | 9/2014 | Estmer Nilsson | ... C12Q 1/6806 435/6.12 |

FOREIGN PATENT DOCUMENTS

| | | |
|---|---|---|
| CN | 103834637 A | 6/2014 |
| EP | 0389063 A2 | 3/1990 |

(Continued)

OTHER PUBLICATIONS

Boom et al., "Rapid and Simple Method for Purification of Nucleic Acids," Journal of Clinical Microbiology, 28(3), 495-503 (Mar. 1990).*
Den Dulk et al., "Magneto-capillary Valve for Integrated Purification and Enrichment of Nucleic Acids and Proteins," Lab on a Chip, 13, 106-118 (2013).*
Den Dulk, Remco C., et al. "Magneto-capillary valve for integrated purification and enrichment of nucleic acids and proteins." Lab on a Chip 13.1 (2013): 106-118.*
GeneCatcher gDNA BLook Kits, "User Guide Life", Invitrogent, 2012.
Boom et al. "Rapid and Simple Method for Purification of Nucleic Acids", Journal of Clinical Microbiology, vol. 28, 1990, pp. 495-503.

(Continued)

*Primary Examiner* — Patrick T Lewis (57) ABSTRACT

A simplified method of obtaining purified nucleic acids uses a single buffer solution to both wash and elute nucleic acids bound to a binding phase. Use of a single buffer solution avoids the time-consuming aspect of using different wash and elution buffer solutions during multiple nucleic acid purification steps. The method for purifying nucleic acids using a single buffer solution includes steps of:
  exposing a sample comprising nucleic acids to a nucleic acid binding phase, where the nucleic acid binding phase may include magnetic particles, silica particles, or a mixture thereof; and allowing the nucleic acids to bind to the nucleic acid binding phase;
  washing the nucleic acids bound to the nucleic acid binding phase at least once with the single buffer solution at room temperature; and
  eluting the nucleic acids from the nucleic acid binding phase with ≤50 μl of the single buffer solution, at a temperature of ≥40° Celsius.

17 Claims, 2 Drawing Sheets

(56) References Cited

FOREIGN PATENT DOCUMENTS

| EP | 0967218 A1 | 12/1999 |
|----|------------|---------|
| EP | 1767621 A1 | 3/2007 |
| JP | 2013217699 A | 10/2013 |
| WO | 2008000343 A1 | 1/2008 |
| WO | 2014066376 A1 | 5/2014 |

OTHER PUBLICATIONS

Den Dulk et al "Magneto-Capillary Valve for Integrated Purification and Enrichment of Nucleic Acids and Proteins", Lab Chip, vol. 13, pp. 106-118, 2013.
NucliSens easyMAG, Biomerieux Industry 2006.
"QIAamp DNA Mini and Blood Mini Handbook", Jun. 2012, Third Edition, Qiagen.
Boom, Rene et al "Improved Silica-Guanidiniumthiocyanate DNA Isolation Procedure based on Selective binding of Bovine Alpha-Casein to Silica Particles", Journal of Clinical Microbiology, vol. 37, No. 3, pp. 615-619, 1999.
Saliva DNA Isolation Kit—50 Preps Product Insert // Norgen Biotek Corp, p. 1-6, :[https://norgenbiotek.com/sites/default/files/resources/Saliva-DNA-Isolation-Kit-PIRU45400-4-M14.pdf] (2014).

\* cited by examiner

NUCLEIC ACID PURIFICATION SYSTEM USING A SINGLE WASH AND ELUTION BUFFER SOLUTION

This invention was made with US Government support under HR0011-12-C-0007 awarded by the Defense Advanced Research Projects Agency. The US Government has certain rights in this invention.

CROSS-REFERENCE TO PRIOR APPLICATIONS

This application is the U.S. National Phase application under 35 U.S.C. § 371 of International Application No. PCT/EP2016/082733, filed on Dec. 27, 2016, which claims the benefit of European Patent Application No. 15202803.1, filed on Dec. 28, 2015. These applications are hereby incorporated by reference herein.

FIELD OF THE INVENTION

The present invention relates to methods or kits for purifying nucleic acids using a single wash and elution buffer solution, and more specifically in a miniaturized setting. The present invention further relates to the use of a buffer solution having a low salt concentration and relatively high pH for purifying nucleic acids.

BACKGROUND OF THE INVENTION

Nucleic acids play an important role in many different fields of research. In industrial settings nucleic acids may be detected within product quality management and in clinical settings nucleic acids may be used for diagnosis and/or for therapy. Prior to their use in many of the afore-mentioned applications, nucleic acids need to be purified.

Nucleic acid purification usually comprises several steps such as exposing a sample containing nucleic acids and selectively binding the nucleic acids to a nucleic acid binding phase, purifying the bound nucleic acids from impurities and obtaining the purified nucleic acids. Different buffers are commonly used during sample preparation, nucleic acid binding, washing and elution steps.

The most commonly used purification methods achieve binding/washing and subsequent elution of nucleic acids either based on a change of pH or based on a change of salt concentrations by using different buffers.

Qiagen's ChargeSwitch® technology is for example based on binding and washing negatively charged nucleic acids on a nucleic acid binding phase, which is positively charged when immersed in buffer solution of pH<6.5. For elution of the nucleic acids a buffer solution of pH 8.5 is used, leading to an increase in pH and the neutralization of the positive charge of the nucleic acid binding phase, thus, resulting in release of the bound nucleic acids.

Another commonly used method, which was developed by Boom et al. (EP 0 389 063) is based on lysis and binding of nucleic acids to a nucleic acid binding phase, e.g. diatoms, glass or silica in the presence of high concentrations of a chaotropic salt, e.g. guanidinium thiocyanate, which allow positively charged ions to form salt bridges between the negatively charged nucleic acids and the negatively charged binding phase. Bound nucleic acids are initially washed in the presence of high salt buffer solutions, then with alcohol-water solutions and eluted by switching to a low salt non-alcohol buffer solution such as TE buffer.

As outlined above, current nucleic acid purification methods comprise multiple washing steps followed by an elution step using a multitude of buffers characterized by different salt concentrations and/or a different pH, which render these methods time-consuming and costly.

Furthermore, remains of the binding and washing buffer solutions are sometimes difficult to remove during the final elution step and may subsequently interfere with downstream procedures such as PCR analysis or sequencing reactions.

SUMMARY OF THE INVENTION

There is hence a need for improved means and methods for simplified, fast, low-cost and efficient purification of nucleic acids.

Existing methods for nucleic acid purification are laborious and time-consuming since they comprise multiple washing steps, often using different washing buffers, followed by an ultimate step of eluting the bound nucleic acids using elution buffer.

The present invention solves this problem by providing a method for purifying nucleic acids comprising the steps of (i) exposing a sample comprising nucleic acids to a nucleic acid binding phase and allowing the nucleic acids to bind to the nucleic acid binding phase, (ii) washing the nucleic acids bound to the nucleic acid binding phase at least once with a buffer solution comprising a buffering agent, (iii) eluting the nucleic acids from the nucleic acid binding phase using the buffer solution of step (ii).

An object of the present invention is to achieve simplified and fast purification of nucleic acids in high amounts. In particular, these high amounts generally improves existing nucleic acid purification methods which are generally designed to be carried out in large volumes (elution volumes of $\geq 50$ μl) which might be a disadvantage for certain applications.

According to the present invention, this can be achieved by a method employing a single buffer solution for washing nucleic acids bound to a nucleic acid binding phase and subsequently eluting these nucleic acids from the nucleic acid binding phase.

An advantage of the method according to the present invention is that only one buffer needs to be provided in order to carry out the method, as opposed to different buffers for washing and for eluting the sample, as described in the prior art. This in turns results into a more simplified method as opposed to the prior art, and hence more economical and more reproducible.

According to the present invention, this can also be achieved by using a single buffer solution for washing and eluting nucleic acids, which is characterized by a relatively low salt concentration of $\leq 100$ mM, and a relatively high pH of $\geq 7.5$.

An advantage of the single buffer according to the present invention is that it is possible to achieve high elution efficiency by employing very small volumes of said buffer; moreover, by using one single buffer it is possible to achieve a faster processing of nucleic acids, which is particularly advantageous in a miniaturized environment.

According to the present invention, this simplified and fast purification of nucleic acids can further be achieved by a kit comprising a nucleic acid binding phase, a buffer solution comprising a buffering agent for washing and eluting of the nucleic acids or a dry form of said buffer solution, a means for detecting the purified nucleic acids.

According to the present invention, this simplified and fast purification of nucleic acids can further be achieved by a cartridge comprising a first chamber comprising a nucleic acid binding phase, a second chamber, connected to the first chamber, comprising a buffer solution comprising a buffering agent for washing and eluting of the nucleic acids or a dry form of said buffer solution, a third chamber connected to the second chamber, comprising a buffer solution comprising the buffer solution of the second chamber, or a dry form of said buffer solution.

A kit and a cartridge according to the present invention are advantageous in comparison to the prior art in that they are easier to prepare, and hence more economical, in particular for large scale productions. Moreover, by reducing the number of different ingredients comprised in the kit or in the cartridge, intervariability is also sensibly reduced.

An object of the present invention is to achieve nucleic acid wash and elution from a nucleic acid binding phase using a buffer solution of the present invention, which will allow direct and immediate further processing of the purified nucleic acids after elution, e.g. in amplification or sequencing reactions.

Existing methods for nucleic acid purification are difficult to scale down to be carried out in miniaturized environments such as microfluidic devices.

Therefore, an object of the present invention is to achieve efficient nucleic acid purification in miniaturized environments, e.g. with microfluidic devices or with magneto-capillary valves, wherein the wash and elution steps are performed in ≤500 µl or ≤50µ, respectively.

These and other aspects of the invention will be apparent from and elucidated with reference to the embodiment(s) described herein after.

DETAILED DESCRIPTION OF EMBODIMENTS

The present invention describes buffer solutions as well as methods and kits, using a single buffer solution for washing and eluting and thus for highly efficient purification of nucleic acid molecules.

Although the present invention will be described with respect to particular embodiments, this description is not to be construed in a limiting sense.

Before describing in detail exemplary embodiments of the present invention, definitions important for understanding the present invention are given.

As used in this specification and in the claims, the singular form of "a", "an" and "the" also include the respective plurals unless the context clearly dictates otherwise.

It is further to be understood that the terms "comprising", "for example/e.g." and "such as" are not limiting. The term "may" is neither to be understood as compulsory nor as limiting.

The term "optionally" is to be understood as an alternative or a specification. The term "particularly" is to be seen as a preferred embodiment of the present invention.

The term "single buffer solution" or "single wash and elution buffer" as used herein refers to buffer solutions having the same composition, ratio of components and characteristics.

The terms "expose/exposing" and "bind/binding" refer to bringing the sample in contact with a nucleic acid binding phase under conditions where the nucleic acids of the sample are capable of binding to a nucleic acid binding phase. In certain embodiments of the present invention "bind/binding" means that ≥25% of nucleic acids present in a sample are bound, or ≥50%, or ≥75%, or ≥85% or ≥95% of nucleic acids present in a sample are bound.

The terms "wash/washing" or "wash/washing step" refer to a situation following binding, in which impurities such as debris, e.g. organelles, parts of cell walls or bacterial or viral particles, proteins and/or remnants, e.g. salt or detergent from lysis or binding procedures are to a large extent removed from nucleic acids bound to a nucleic acid binding phase. In certain embodiments of the present invention "wash/washing" or "wash/washing step" mean that ≤25% of nucleic acids bound to a nucleic acid binding phase are removed, or ≤20%, or ≤15%, or ≤10%, or ≤5% of nucleic acids bound to a nucleic acid binding phase are removed.

The terms "elute/eluting" or "elution step" refer to conditions under which the bound nucleic acids are finally released from a nucleic acid binding phase. In certain embodiments of the present invention "elute/eluting" or "elution step" mean that ≥25% of nucleic acids initially bound to a nucleic acid binding phase are eluted, or ≥35%, or ≥45%, or ≥55%, or ≥65%, or ≥75%, or ≥85% or ≥95% of nucleic acids initially bound to a nucleic acid binding phase are eluted.

In certain embodiments of the present invention "wash/washing" or "wash/washing step" mean that ≤25% of nucleic acids bound to a nucleic acid binding phase are removed, or ≤20%, or ≤15%, or ≤10%, or ≤5% of nucleic acids bound to a nucleic acid binding phase are removed and "elute/eluting" or "elution step" mean that ≥25% of nucleic acids initially bound to a nucleic acid binding phase are eluted, or ≥35%, or ≥45%, or ≥55%, or ≥65%, or ≥75%, or ≥85% or ≥95% of nucleic acids initially bound to a nucleic acid binding phase are eluted.

"Room temperature" as used herein refers to temperatures of 18° to 26° Celsius, preferably 20° to 23° Celsius.

The symbol "~" as used herein typically indicates a deviation from the indicated numerical value of ±20%, preferably ±15%, more preferably ±10%, and even more preferably ±5%.

The present invention provides a method for purifying nucleic acids comprising the steps of
(i) exposing a sample comprising nucleic acids to a nucleic acid binding phase and allowing the nucleic acids to bind to the nucleic acid binding phase,
(ii) washing the nucleic acids bound to the nucleic acid binding phase at least once with a buffer solution comprising a buffering agent,
(iii) eluting the nucleic acids from the nucleic acid binding phase using the buffer solution of step (ii).
In one embodiment of the present invention, the method for purifying nucleic acids comprises the steps of
(i) exposing a sample comprising nucleic acids to a nucleic acid binding phase and allowing the nucleic acids to bind to the nucleic acid binding phase,
(ii) washing the nucleic acids bound to the nucleic acid binding phase at least once with a buffer solution,
(iii) eluting the nucleic acids from the nucleic acid binding phase using the buffer solution of step (ii),
wherein no further step or steps are carried out between steps (i) and (ii).

In another embodiment of the present invention, the method for purifying nucleic acids comprises the steps of
(i) exposing a sample comprising nucleic acids to a nucleic acid binding phase and allowing the nucleic acids to bind to the nucleic acid binding phase,
(ii) washing the nucleic acids bound to the nucleic acid binding phase at least once with a buffer solution comprising a buffering agent,
(iii) eluting the nucleic acids from the nucleic acid binding phase using the buffer solution of step (ii),
wherein no further step or steps are carried out between steps (ii) and (iii).

In a further embodiment of the present invention, the method for purifying nucleic acids comprises the steps of
(i) exposing a sample comprising nucleic acids to a nucleic acid binding phase and allowing the nucleic acids to bind to the nucleic acid binding phase,
(ii) washing the nucleic acids bound to the nucleic acid binding phase at least once with a buffer solution comprising a buffering agent,
(iii) eluting the nucleic acids from the nucleic acid binding phase using the buffer solution of step (ii),
wherein no further steps are carried out between steps (i) and (ii) and between the steps (ii) and (iii).

In one embodiment of the present invention the method for purifying nucleic acids consists of the steps of
(i) exposing a sample comprising nucleic acids to a nucleic acid binding phase and allowing the nucleic acids to bind to the nucleic acid binding phase,
(ii) washing the nucleic acids bound to the nucleic acid binding phase at least once with a buffer solution comprising a buffering agent,
(iii) eluting the nucleic acids from the nucleic acid binding phase using the buffer solution of step (ii).

In the context of the present invention using the buffer solution of step (ii) in step (iii) of the method of the invention means using buffer solutions having the same composition, ratio of components and characteristics in steps (ii) and (iii) of the method of the invention. To simplify matters the term "single buffer solution" or "single wash and elution buffer solution" will be used throughout the application to depict the buffer solution used in step (ii) and (iii) of the method of the invention.

Using a single buffer solution for washing and elution of nucleic acids, optionally in a method as described in the embodiments of the invention or as provided by the kit of the invention renders purification of nucleic acids fast, simple and cost-effective.

Exposing a sample comprising nucleic acids and binding the nucleic acids to a nucleic acid binding phase may be achieved by adding a sample to a nucleic acid binding phase and optionally letting the sample pass through or flow by a nucleic acid binding phase. Exposition may also be achieved by immersing, resuspending or mixing the sample with a nucleic acid binding phase. The sample may be incubated on or with the nucleic acid binding phase for 1 to 30 minutes at room temperature and a pH of 4 to 8 with any suitable buffer solution for binding. Nucleic acids may be bound in the presence of or without chaotropic substances, e.g. guanidinium (iso)thiocyanate, guanidine hydrochloride, sodium iodide, potassium iodide, sodium (iso)thiocyanate, urea or combinations thereof.

In one embodiment of the present invention, a sample is incubated on or with the nucleic acid binding phase for 1 to 30 minutes at room temperature and a pH of 4.

In another embodiment of the present invention, nucleic acids are bound to a nucleic acid binding phase using a buffer solution containing guanidinium isothiocyanate.

In a further embodiment of the present invention, nucleic acids are bound to a nucleic acid binding phase using a buffer solution containing guanidinium isothiocyanate for 1 to 30 minutes at room temperature and a pH of 4.

In one embodiment of the present invention step (i) of the method of the invention is performed in the presence of high salt concentrations, e.g salt concentrations in the molar and high millimolar range.

In a preferred embodiment of the present invention step (i) of the method of the invention is performed in the presence of high salt concentrations of 1M to 6M.

Ideally, wash buffer solutions remove unwanted cell components such as cell, bacterial, viral debris; proteins as well as residual amounts of for example detergent and chaotropic salts, which might stem from previous lysis or binding steps.

Bound nucleic acids may be washed and eluted using a buffer solution having a salt concentration of ≤500 mM, ≤400 mM, ≤300 mM, ≤200 mM, ≤100 mM, ≤75 mM, ≤50 mM, ≤40 mM, ≤30 mM, ≤20 mM, ≤10 mM, ≤7.5 mM, ≤5 mM, ≤2.5 mM.

In a preferred embodiment of the present invention the buffer solution employed in steps (ii) and (iii) of the method of the invention has a salt concentrations of ≤100 mM, preferably ≤50 mM, more preferably ≤30 mM, most preferably ≤10 mM.

Bound nucleic acids may further be washed and eluted using a buffer solution having a pH of ≥7.5, ≥8, ≥8.5, ≥9, ≥9.5 or ≥10.

In a preferred embodiment of the present invention the buffer solution employed in steps (ii) and (iii) of the method of the invention has a pH value of ≥7.5 or ≥9.

In one embodiment of the present invention the buffer solution employed in steps (ii) and (iii) of the method of the invention has a salt concentration of ≤100 mM, preferably ≤50 mM, more preferably ≤30 mM, most preferably ≤10 mM and a pH of ≥7.5 or ≥9.

In another embodiment of the present invention the buffer solution employed in steps (ii) and (iii) of the method of the invention has a salt concentration of ≤30 mM and a pH of ≥7.5.

In another embodiment of the present invention the buffer solution employed in steps (ii) and (iii) of the method of the invention has a salt concentration of ≤30 mM and a pH of ≥9.

In a further embodiment of the present invention the buffer solution employed in steps (ii) and (iii) of the method of the invention has a salt concentration of ≤10 mM and a pH of ≥7.5.

In a preferred embodiment of the present invention the buffer solution employed in steps (ii) and (iii) of the method of the invention has a salt concentration of ≤10 mM and a pH of ≥9.

In a more preferred embodiment of the present invention the buffer solution employed in steps (ii) and (iii) of the method of the invention has a salt concentration of 10 mM and a pH of ≥7.5.

In a most preferred embodiment of the present invention the buffer solution employed in steps (ii) and (iii) of the method of the invention has a salt concentration of 10 mM and a pH of 9.

Bound nucleic acids may further be washed and eluted using buffering solutions comprising buffering agents, e.g. citrate, malate, formate, citrate, succinate, acetate, propionate, malate, pyridine, cacodylate, succinate, histidine, bis-tris, ethanolamine, ADA, ACES, PIPES, MOPSP, imidazole, BIS-TRIS propane, BES, MOPS, HEPES, TES, MOBS, DIPSO, TAPSO, triethylamine (TEA), pyrophosphate, HEPPSO, Tris-HCl, POPSO, tricine, hydrazine, glycylglycine, Trizma, EPPS, HEPPS, BICINE HEPBS, TAPS, 2-amino-2-methyl-1,3-propanediol (AMPD), TABS, AMPSO, taurine (AES), borate, CHES, 2-amino-2-methyl-1-propanol (AMP), glycine, ammonium hydroxide, CAPSO, carbonate, methylamine, piperazine, CAPS and phosphate.

Bound nucleic acids may preferably be washed and eluted using buffering solutions comprising buffering agents, e.g. DIPSO, TAPSO, triethylamine (TEA), pyrophosphate, HEPPSO, Tris-HCl, POPSO, tricine, hydrazine, glycylglycine, Trizma, EPPS, HEPPS, BICINE HEPBS, TAPS, 2-amino-2-methyl-1,3-propanediol (AMPD), TABS, AMPSO, taurine (AES), borate, CHES, 2-amino-2-methyl-1-propanol (AMP), glycine, ammonium hydroxide, CAPSO, carbonate, methylamine, piperazine, CAPS and phosphate, MES (2-(N-morpholino)ethanesulfonic acid) or TE (Tris-EDTA).

Bound nucleic acids may most preferably be washed and eluted using buffer solutions comprising buffering agents with a buffering range of pH 7 to 11, e.g. DIPSO, TAPSO, triethylamine (TEA), pyrophosphate, HEPPSO, Tris-HCl, POPSO, tricine, hydrazine, glycylglycine, Trizma, EPPS, HEPPS, BICINE HEPBS, TAPS, 2-amino-2-methyl-1,3-propanediol (AMPD), TABS, AMPSO, taurine (AES), borate, CHES, 2-amino-2-methyl-1-propanol (AMP), glycine, ammonium hydroxide, CAPSO, carbonate, methylamine, piperazine, CAPS, phosphate and TE.

In one embodiment of the present invention the buffering agent in the buffer solution employed in steps (ii) and (iii) of the method of the invention is TE or Tris-HCl.

In another embodiment of the present invention the buffering agent in the buffer solution employed in steps (ii) and (iii) of the method of the invention is Tris-HCl.

In another embodiment of the present invention the buffer solution employed in steps (ii) and (iii) of the method of the invention has a Tris-HCl concentration of ≤100 mM, preferably ≤50 mM, more preferably ≤30 mM, most preferably ≤10 mM.

In a further embodiment of the present invention the buffering agent of the buffer solution employed in steps (ii) and (iii) of the method of the invention is Tris-HCl and the buffering solution has a pH of ≥7.5 or preferably ≥9.

In a preferred embodiment of the present invention the buffer solution employed in steps (ii) and (iii) of the method of the invention has a Tris-HCl concentration of ≤100 mM, preferably ≤50 mM, more preferably ≤30 mM, most preferably ≤10 mM and a pH of ≥7.5 or preferably ≥9.

In another preferred embodiment of the present invention the buffer solution employed in steps (ii) and (iii) of the method of the invention has a Tris-HCl concentration of ≤30 mM and a pH of ≥7.5.

In a further preferred embodiment of the present invention the buffer solution employed in steps (ii) and (iii) of the method of the invention has a Tris-HCl concentration of ≤30 mM and a pH of ≥9.

In a more preferred embodiment of the present invention the buffer solution employed in steps (ii) and (iii) of the method of the invention has a Tris-HCl concentration of ≤10 mM and a pH of ≥7.5.

In an even more preferred embodiment of the present invention the buffer solution employed in steps (ii) and (iii) of the method of the invention has a Tris-HCl concentration of ≤10 mM and a pH of ≥9.

In a most preferred embodiment of the present invention the buffer solution employed in steps (ii) and (iii) of the method of the invention has a Tris-HCl concentration of 10 mM and a pH of ≥7.5.

In an utmost preferred embodiment of the present invention the buffer solution employed in steps (ii) and (iii) of the method of the invention has a Tris-HCl concentration of 10 mM and a pH of 9.

In one embodiment of the present invention step (ii) of the method of the invention is performed in ≤500 μl, ≤400 μl, ≤300 μl, ≤200 μl, ≤100 μl, ≤50 μl or ≤20 μl of buffer solution.

In another embodiment of the present invention step (ii) of the method of the invention is performed in ≤50 μl or ≤20 μl of buffer solution.

In a further embodiment of the present invention step (ii) of the method of the invention is performed in ≤50 μl or ≤20 μl of a buffer solution, having a salt concentration of ≤100 mM, preferably ≤50 mM, more preferably ≤30 mM, most preferably ≤10 mM.

In another embodiment of the present invention step (ii) of the method of the invention is performed in ≤50 μl or ≤20 μl of a buffer solution, having a pH of ≥7.5 or ≥9.

In a preferred embodiment step (ii) of the method of the invention is performed in ≤50 μl or ≤20 μl of a buffer solution, having a salt concentration of ≤100 mM, preferably ≤50 mM, more preferably ≤30 mM, most preferably ≤10 mM and a pH of ≥7.5 or ≥9.

In another preferred embodiment of the present invention step (ii) of the method of the invention is performed in ≤20 μl of buffer solution.

In a further preferred embodiment of the present invention step (ii) of the method of the invention is performed in ≤20 μl of a buffer solution, having a salt concentration of ≤30 mM and a pH of ≥7.5.

In another preferred embodiment of the present invention step (ii) of the method of the invention is performed in ≤20 μl of a buffer solution, having a salt concentration of ≤30 mM and a pH of ≥9.

In most preferred embodiment of the present invention step (ii) of the method of the invention is performed in ≤20 μl of a buffer solution, having a salt concentration of ≤10 mM and a pH of ≥7.5.

In another most preferred embodiment of the present invention step (ii) of the method of the invention is performed in ≤20 µl of a buffer solution, having a salt concentration of ≤10 mM and a pH of ≥9.

In an utmost preferred embodiment of the present invention step (ii) of the method of the invention is performed in ≤20 µl of a buffer solution, having a salt concentration of 10 mM and a pH of 9.

According to one embodiment of the present invention, the buffering agent of the buffer solution of the immediate above embodiments is Tris-HCl.

In one embodiment of the present invention bound nucleic acids are washed at least once in step (ii) of the method of the invention.

In a preferred embodiment, bound nucleic acids are washed at least twice, preferably twice in step (ii) of the method of the present invention.

In a more preferred embodiment of the present invention bound nucleic acids are washed twice in step (ii) of the method, wherein step (ii) is performed in ≤20 µl of a buffer solution, having a salt concentration of ≤10 mM and a pH of ≥9.

In a most preferred embodiment of the present invention bound nucleic acids are washed twice in step (ii), wherein step (ii) is performed in ≤20 µl of a buffer solution, having a salt concentration of 10 mM and a pH of 9.

In another most preferred embodiment of the present invention bound nucleic acids are washed twice in step (ii), wherein step (ii) is performed in ≤20 µl of a buffer solution, having a Tris-HCl concentration of 10 mM and a pH of 9.

In one embodiment of the present invention step (iii) of the method of the invention is performed in ≤50 µl, ≤40 µl, ≤30 µl, ≤20 µl, ≤15 µl, ≤10 µl or ≤5 µl of buffer solution.

In another embodiment of the present step (iii) of the method of the invention is performed in ≤5 µl of buffer solution.

In one embodiment of the present invention step (ii) of the method of the invention is performed in ≤500 µl, ≤400 µl, ≤300 µl, ≤200 µl, ≤100 µl, ≤50 µl or ≤20 µl and step (iii) of the method of the invention is performed in ≤50 µl, ≤40 µl, ≤30 µl, ≤20 µl, ≤15 µl, ≤10 µl, ≤5 µl of buffer solution.

In another embodiment of the present invention step (ii) of the method of the
invention is performed in ≤500 µl, ≤400 µl, ≤300 µl, ≤200 µl, ≤100 µl, ≤50 µl or ≤20 µl and step (iii) is performed in ≤50 µl, ≤40 µl, ≤30 µl, ≤20 µl, ≤15 µl, ≤10 µl or ≤5 µl, wherein the buffer solution used in steps (ii) and (iii) has a salt concentration of ≤100 mM, preferably ≤50 mM, more preferably ≤30 mM, most preferably ≤10 mM.

In a further embodiment of the present invention step (ii) of the method of the invention is performed in ≤500 µl, ≤400 µl, ≤300 µl, ≤200 µl, ≤100 µl, ≤50 µl or ≤20 µl and step (iii) is performed in ≤50 µl, ≤40 µl, ≤30 µl, ≤20 µl, ≤15 µl, ≤10 µl or ≤5 µl, wherein the buffer solution used in steps (ii) and (iii) has a pH of ≥7.5 or ≥9.

In one embodiment of the present invention step (ii) of the method of the invention is performed in ≤500 µl, ≤400 µl, ≤300 µl, ≤200 µl, ≤100 µl, ≤50 µl or ≤20 µl and step (iii) is performed in ≤50 µl, ≤40 µl, ≤30 µl, ≤20 µl, ≤15 µl, ≤10 µl or ≤5 µl, wherein the buffer solution used in steps (ii) and (iii) has a salt concentration of ≤100 mM, preferably ≤50 mM, more preferably ≤30 mM, most preferably ≤10 mM and a pH of ≥7.5 or ≥9.

In a preferred embodiment of the present invention step (ii) of the method of the invention is performed in ≤20 µl and step (iii) is performed in ≤5 µl, wherein the buffer solution used in steps (ii) and (iii) has a salt concentration of ≤100 mM, preferably ≤50 mM, more preferably ≤30 mM, most preferably ≤10 mM and a pH of ≥7.5 or ≥9.

In another preferred embodiment of the present invention step (ii) of the method of the invention is performed in ≤20 µl and step (iii) is performed in ≤5 µl, wherein the buffer solution used in steps (ii) and (iii) has a salt concentration of ≤30 mM and a pH of ≥9.

In a most preferred embodiment of the present invention step (ii) of the method of the invention is performed in ≤20 µl and step (iii) is performed in ≤5 µl, wherein the buffer solution used in steps (ii) and (iii) has a salt concentration of ≤10 mM and a pH of ≥7.5.

In another most preferred embodiment of the present invention step (ii) of the method of the invention is performed in ≤20 µl and step (iii) is performed in ≤5 µl, wherein the buffer solution used in steps (ii) and (iii) has a salt concentration of ≤10 mM and a pH of ≥9.

In an utmost preferred embodiment of the present invention step (ii) of the method of the invention is performed in ≤20 µl and step (iii) is performed in ≤5 µl, wherein the buffer solution used in steps (ii) and (iii) has a salt concentration of 10 mM and a pH of 9.

In a further preferred embodiment of the present invention step (ii) of the method of the invention is performed in ≤20 µl and step (iii) is performed in ≤5 µl, wherein the buffer solution used in steps (ii) and (iii) has a Tris-HCl concentration of ≤30 mM and a pH of ≥7.5.

In another preferred embodiment of the present invention step (ii) of the method of the invention is performed in ≤20 µl and step (iii) is performed in ≤5 µl, wherein the buffer solution used in steps (ii) and (iii) has a Tris-HCl concentration of ≤30 mM and a pH of ≥9.

In a most preferred embodiment of the present invention step (ii) of the method of the invention is performed in ≤20 µl and step (iii) is performed in ≤5 µl, wherein the buffer solution used in steps (ii) and (iii) has a Tris-HCl concentration of ≤10 mM and a pH of ≥7.5.

In another most preferred embodiment of the present invention step (ii) of the method of the invention is performed in ≤20 µl and step (iii) is performed in ≤5 µl, wherein the buffer solution used in steps (ii) and (iii) has a Tris-HCl concentration of ≤10 mM and a pH of ≥9.

In an utmost preferred embodiment of the present invention step (ii) of the method of the invention is performed in ≤20 µl and step (iii) is performed in ≤5 µl, of wherein the buffer solution used in steps (ii) and (iii) has a Tris-HCl concentration of 10 mM and a pH of 9.

According to one embodiment of the present invention, bound nucleic acids are washed at least twice, preferably twice in step (ii) of any of the immediate above embodiments of the invention.

According to one embodiment of the present invention, step (i) of the method of the invention may be performed in the presence of high salt concentrations, wherein the bound nucleic acids are washed and eluted as described in the above embodiments.

In one embodiment of the present invention, at least 25%, 50%, 55%, 60%, 65%, 70%, 75%, 80%, 85%, 90%, 95% or 100% of nucleic acids present in the sample comprising nucleic acids are obtained in the eluate of step (iii) of the method of the invention, using the buffer solution of the present invention or with the kit of the present invention.

In another embodiment of the present invention, different nucleic acids are purified simultaneously. A common method of obtaining e.g. RNA or DNA is to add RNAses or DNAses, respectively to the purified nucleic acids.

In a further embodiment of the present invention the sample comprising nucleic acids is lysed prior to step (i) of the method of the invention. Known methods for cell lysis are suitable for use within the invention such as physical disruption, e.g. by blending, grinding, via shearing forces, by sonication, ultrasound, applying pressure, bead beating or freezing and thawing; or chemical disruption, e.g. by chaotropic or kosmotropic salts, detergents such as Triton X, NP40, Tween or SDS; or enzymatic disruption, e.g. by lysozyme, proteinase K or subtilisin.

In one embodiment of the present invention the sample comprising nucleic acids is not lysed by chaotropic salts or detergents.

In another embodiment of the present invention the sample comprising nucleic acids is lysed by kosmotropic salts.

In a preferred embodiment of the present invention the sample comprising nucleic acids is lysed prior to step (i) of the method of the invention; step (ii) of the method of the invention is performed in ≤500 μl, ≤400 μl, ≤300 μl, ≤200 μl, ≤100 μl, ≤50 μl or ≤20 μl and step (iii) of the method of the invention is performed in ≤50 μl, ≤40 μl, ≤30 μl, ≤20 μl, ≤15 μl, ≤10 μl or ≤5 μl of buffer solution.

In another preferred embodiment of the present invention the sample comprising nucleic acids is lysed prior to step (i) of the method of the invention; step (ii) of the method of the invention is performed in ≤500 μl, ≤400 μl, ≤300 μl, ≤200 μl, ≤100 μl, ≤50 μl or ≤20 μl and step (iii) is performed in ≤50 μl, ≤40 μl, ≤30 μl, ≤20 μl, ≤15 μl, ≤10 μl or ≤5 μl, wherein the buffer solution used in steps (ii) and (iii) has a salt concentration of ≤100 mM, preferably ≤50 mM, more preferably ≤30 mM, most preferably ≤10 mM.

In a further preferred embodiment of the present invention the sample comprising nucleic acids is lysed prior to step (i) of the method of the invention; step (ii) of the method of the invention is performed in ≤500 μl, ≤400 μl, ≤300 μl, ≤200 μl, ≤100 μl, ≤50 μl or ≤20 μl and step (iii) is performed in ≤50 μl, ≤40 μl, ≤30 μl, ≤20 μl, ≤15 μl, ≤10 μl or ≤5 μl, wherein the buffer solution used in steps (ii) and (iii) has a pH of ≥7.5 or ≥9.

In a more preferred embodiment of the present invention the sample comprising nucleic acids is lysed prior to step (i) of the method of the invention; step (ii) of the method of the invention is performed in ≤20 μl and step (iii) is performed in ≤5 wherein the buffer solution used in steps (ii) and (iii) has a salt concentration of ≤100 mM, preferably ≤50 mM, more preferably ≤30 mM, most preferably ≤10 mM and a pH of ≥7.5 or ≥9.

In a further more preferred embodiment of the present invention the sample comprising nucleic acids is lysed prior to step (i) of the method of the invention; step (ii) of the method of the invention is performed in ≤20 μl and step (iii) is performed in ≤5 μl, wherein the buffer solution used in steps (ii) and (iii) has a salt concentration of ≤30 mM and a pH of ≥7.5.

In another more preferred embodiment of the present invention the sample comprising nucleic acids is lysed prior to step (i) of the method of the invention; step (ii) of the method of the invention is performed in ≤20 μl and step (iii) is performed in ≤5 μl, wherein the buffer solution used in steps (ii) and (iii) has a salt concentration of ≤30 mM and a pH of ≥9.

In a most preferred embodiment of the present invention the sample comprising nucleic acids is lysed prior to step (i) of the method of the invention; step (ii) of the method of the invention is performed in ≤20 μl and step (iii) is performed in ≤5 μl, wherein the buffer solution used in steps (ii) and (iii) has a salt concentration of ≤10 mM and a pH of ≥7.5.

n another most preferred embodiment of the present invention the sample comprising nucleic acids is lysed prior to step (i) of the method of the invention; step (ii) of the method of the invention is performed in ≤20 μl and step (iii) is performed in ≤5 μl, wherein the buffer solution used in steps (ii) and (iii) has a salt concentration of ≤10 mM and a pH of ≥9.

In an utmost preferred embodiment of the present invention the sample comprising nucleic acids is lysed prior to step (i) of the method of the invention; step (ii) of the method of the invention is performed in ≤20 μl and step (iii) is performed in ≤5 μl, wherein the buffer solution used in steps (ii) and (iii) has a salt concentration of 10 mM and a pH of 9.

According to one embodiment of the present invention, the buffering agent in the buffering solution of the immediate above embodiments is Tris-HCl.

According to another embodiment of the present invention, bound nucleic acids are washed at least twice, preferably twice in step (ii) of the method of the invention in any of the immediate above embodiments of the invention.

According to yet another embodiment of the present invention step (i) of the method of the invention is performed in the presence of high salt concentrations, wherein the bound nucleic acids are washed (step (ii)) and eluted (step (iii)) as described in the above embodiments.

Samples comprising nucleic acids as used herein comprise biological samples, e.g. bacteria, yeast, viruses, eukaryotic cells, animal cells, mammalian cells, human cells, whole blood, blood serum, platelet-rich plasma, buffy coat, samples from nasal, oral, vaginal or rectal swabs, nasopharyngeal or bronchial aspirates and washes, cerebrospinal fluid, saliva, feces, urine, semen and tissue. Samples comprising nucleic acids may also be laboratory samples such as amplification reactions mixtures and (melted) agarose gel probes. Samples comprising nucleic acids may further be food or soil samples. If applicable, samples may have been dissolved, partially clarified or purified for example by centrifugation, precipitation and/or filtration.

In an embodiment of the present invention the sample comprising nucleic acids comprises eukaryotic cells, preferably human cells, more preferably epithelial cells.

In a preferred embodiment of the present invention the sample comprising nucleic acids comprises epithelial cells.

In another embodiment of the present invention a sample comprising nucleic acids further comprises bacteria and/or viruses.

Bacteria may for example comprise *Bacillus, Bartonella, Bordetella, Borrelia, Brucella, Campylobacter, Chlamydia, Clostridium, Corynebacterium*, e.g. *Corynebacterium diptheriae, Enterococcus, Escherichia, Francisella, Haemophilus, Heliobacter, Legionella, Leptospira, Listeria, Mycobacterium, Mycoplasma, Neisseria, Pseudomonas, Rickettsia, Staphylococcus, Salmonella, Shigella, Streptococcus, Treponema, Ureaplasma, Vibrio* or *Yersinia*. Viruses may for example comprise Epstein-Barr virus, Hepatitis virus, Herpes virus, human immunodeficiency virus, human papillomavirus, Filovirus, Influenza virus or Rabies virus.

Nucleic acids to be purified by the method of the invention comprise deoxyribonucleic acid (DNA), ribonucleic acid (RNA) and hybrids thereof. DNA and RNA may exist single and double stranded.

DNA may be present as genomic DNA, cDNA or in circular form such as supercoiled, coiled and relaxed plasmid DNA and may further be present as A-DNA, B-DNA or Z-DNA.

The term "RNA" includes bacterial RNA, viral RNA, retroviral RNA, messenger RNA (mRNA), ribosomal RNA (rRNA), ribozymes, aptamers, riboswitches, transfer RNA (tRNA), small interfering RNA (siRNA), antisense RNA, small nuclear RNA (snRNA), small nucleolar RNA (snoRNA), microRNA (miRNA), Piwi-interacting (piRNA), CRISPR RNA and immunostimulating RNA. DNA and RNA may exist in different length, e.g. from ≤0.05 kb to ≥100 kb.

Nucleic acids to be purified also comprise nucleic acids modified in a sugar moiety, a phosphate backbone or a base moiety.

Nucleic acids to be purified further comprise synthesized nucleic acids, e.g. in vitro transcribed RNA (in vitro RNA), optionally fluorescently or radioactively labeled.

In a preferred embodiment of the invention the nucleic acids to be purified are viral DNA or viral RNA.

Nucleic acid binding phases as used within the method of the present invention comprise soluble or solid, porous or non-porous substrates capable of binding nucleic acids.

The afore-mentioned substrates may comprise functional chemical groups, e.g. amine groups or amine-functionalized groups. Preferred substrates are diatoms, glass, silicone, silica and substrates coated with silane, optionally containing functional groups, e.g. polyethyleneglycol, amine, epoxide, isothiocyanate as well as substrates coated with poly-L-lysine or polymers, e.g. nitrocellulose, polystyrene, cyclic olefin copolymers (COCs), cyclic olefin polymers (COPs), polypropylene, polyethylene or polycarbonate. The functionalized silanes may be branched or unbranched.

One embodiment of the present invention provides for a nucleic acid binding phase comprising silica.

A further embodiment of the present invention provides for a nucleic acid binding phase comprising silane.

An example for a solid nucleic acid binding substrate are magnetic particles, which are particularly advantageous with regard to handling since they can be used in small amounts and be easily and quantitatively recovered (US 2014/0272999). The magnetic particles may consist of iron, iron oxide, silica, silicon oxide including amorphous silicon oxide, glass powder, quarz, diatomaceous earth, alkyl silica, zeolite, latex particles or polymers, e.g. nitrocellulose, polystyrene, cyclic olefin copolymers (COCs), cyclic olefin polymers (COPs), polypropylene, polyethylene or polycarbonate or be coated with silane, optionally containing functional groups, e.g. polyethyleneglycol, amine, epoxide or isothiocyanate or be coated with L-lysine.

In one embodiment of the present invention, magnetic particles may comprise iron, iron oxide, silica, silicon oxide including amorphous silicon oxide, glass powder, quarz, diatomaceous earth, alkyl silica, zeolite, latex particles or be coated with silane, optionally containing functional groups, e.g. polyethyleneglycol, amine, epoxide or isothiocyanate or be coated with L-lysine.

Magnetic particle size may range between 0.05 μm to 500 μm. Preferred particle sizes range between 1 μm to 200 μm.

In a preferred embodiment of the present invention the nucleic acid binding phase comprises magnetic particles. In an even more preferred embodiment of the present invention, those magnetic particles are coated with silica. In an equally preferred embodiment of the present invention the magnetic particles are coated with silane.

In a preferred embodiment of the present invention, the nucleic acid binding phase comprises negatively charged particles, more preferably magnetic negatively charged particles, wherein the particles may comprise glass, silica, derivatives of silica or be coated with silica, and the nucleic acids bind the nucleic acid binding phase in the presence of high concentrations of a chaotropic salt.

A miniaturized environment in the sense of the present invention refers to a submilliliter space. An example for such a miniaturized environment is a microfluidic device, which is characterized by the engineered manipulation of fluids in a submilliliter space allowing precise control and manipulation of these fluids. Typically, a microfluidic device implements small volumes, e.g. in the μl range and/or it may implement a small overall size. Furthermore, a microfluidic device according to the present invention may be disposable or reusable and consume a low amount of energy. In a microfluidic device effects such as laminar flow, specific surface tensions, electrowetting, fast thermal relaxation, the presence of electrical surface charges and diffusion may be implemented. In certain embodiments, a microfluidic device may have connections with external sources or external elements, e.g. separation or reservoirs or vessels for reuse purposes. Furthermore, the microfluidic device may comprise an electronic or computer interface allowing the control and manipulation of activities in the device, and/or the detection or determination of reaction outcomes or products. Microfluidic devices may be operated manually or automatically e.g. as part of a lab-on-chip approach with all reagents already present in the device.

Microfluidic devices comprise the terms "magneto-capillary valve" or "magneto-capillary valve cartridge" which consist of two planar surfaces at a mutual distance so that discrete units of liquid can be confined at fixed positions in the device by capillary force. The liquid units inside the device may be separated by gas or phase change material such as paraffin that can be melted and solidified based on the applied temperature. Magnetic particles might for example be transferred from one liquid unit to another by magnetic forces (den Dulk, Lab Chip, 2013).

One embodiment of the present invention envisions that the method of the invention is performed with a microfluidic device.

In a further embodiment of the present invention step (ii) of the method of the invention is performed in ≤500 μl, ≤400 μl, ≤300 μl, ≤200 μl, ≤100 μl, ≤50 μl or ≤20 μl and step (iii) of the method of the invention is performed in ≤50 μl, ≤40 μl, ≤30 μl, ≤20 μl, ≤15 μl, ≤10 μl or ≤5 μl of buffer solution with a microfluidic device.

In another embodiment of the present invention step (ii) of the method of the invention is performed in ≤500 μl, ≤400 μl, ≤300 μl, ≤200 μl, ≤100 μl, ≤50 μl or ≤20 μl and step (iii) is performed in ≤50 μl, ≤40 μl, ≤30 μl, ≤20 μl, ≤15 μl, ≤10 μl or ≤5 μl, wherein the buffer solution used in steps (ii) and (iii) has a salt concentration of ≤100 mM, preferably ≤50 mM, more preferably ≤30 mM, most preferably ≤10 mM, with a microfluidic device.

In a further embodiment of the present invention step (ii) of the method of the invention is performed in ≤500 μl, ≤400 μl, ≤300 μl, ≤200 μl, ≤100 μl, ≤50 μl or ≤20 μl and step (iii) is performed in ≤50 μl, ≤40 μl, ≤30 μl, ≤20 μl, ≤15 μl, ≤10 μl or ≤5 μl, wherein the buffer solution used in steps (ii) and (iii) has a pH of ≥7.5 or ≥9, with a microfluidic device.

In a preferred embodiment of the present invention step (ii) of the method of the invention is performed in ≤20 μl and step (iii) is performed in ≤5 μl wherein the buffer solution used in steps (ii) and (iii) has a salt concentration of ≤100 mM, preferably ≤50 mM, more preferably ≤30 mM, most preferably ≤10 mM and a pH of ≥7.5 or ≥9, with a microfluidic device.

In a further preferred embodiment of the present invention step (ii) of the method of the invention is performed in ≤20 μl and step (iii) is performed in ≤5 μl, wherein the buffer solution used in steps (ii) and (iii) has a salt concentration of ≤30 mM and a pH of ≥7.5, with a microfluidic device.

In another preferred embodiment of the present invention step (ii) of the method of the invention is performed in ≤20 µl and step (iii) is performed in ≤5 µl, wherein the buffer solution used in steps (ii) and (iii) has a salt concentration of ≤30 mM and a pH of ≥9, with a microfluidic device.

In a most preferred embodiment of the present invention step (ii) of the method of the invention is performed in ≤20 µl and step (iii) is performed in ≤5 µl, wherein the buffer solution used in steps (ii) and (iii) has a salt concentration of ≤10 mM and a pH of ≥7.5, with a microfluidic device.

In another most preferred embodiment of the present invention step (ii) of the method of the invention is performed in ≤20 µl and step (iii) is performed in ≤5 µl, wherein the buffer solution used in steps (ii) and (iii) has a salt concentration of ≤10 mM and a pH of ≥9, with a microfluidic device.

In an utmost preferred embodiment of the present invention step (ii) of the method of the invention is performed in ≤20 µl and step (iii) is performed in ≤5 µl, wherein the buffer solution used in steps (ii) and (iii) has a salt concentration of 10 mM and a pH of 9, with a microfluidic device.

According to one embodiment of the present invention, the buffering agent in the buffer solution of the immediate above embodiments is Tris-HCl.

According to one embodiment of the present invention, the method of the invention comprises a lysis step prior to step (i) of the method of the invention in any of the above embodiments.

According to one embodiment of the present invention, bound nucleic acids are washed at least twice, preferably twice in step (ii) of the method of the invention in any of the immediate above embodiments of the invention.

In a preferred embodiment of the present invention the method of the invention is performed with a magneto-capillary valve.

In a further embodiment of the present invention bound nucleic acids step (ii) of the method of the invention is performed in ≤500 µl, ≤400 µl, ≤300 µl, ≤200 µl, ≤100 µl, ≤50 µl or ≤20 µl and step (iii) of the method of the invention is performed in ≤50 µl, ≤40 µl, ≤30 µl, ≤20 µl, ≤15 µl, ≤10 µl or ≤5 µl of buffer solution with a magneto-capillary valve.

In another embodiment of the present invention bound nucleic acids are step (ii) of the method of the invention is performed in ≤500 µl, ≤400 µl, ≤300 µl, ≤200 µl, ≤100 µl, ≤50 µl or ≤20 µl and step (iii) is performed in ≤50 µl, ≤40 µl, ≤30 µl, ≤20 µl, ≤15 µl, ≤10 µl or ≤5 µl, wherein the buffer solution used in steps (ii) and (iii) has a salt concentration of ≤100 mM, preferably ≤50 mM, more preferably ≤30 mM, most preferably ≤10 mM, with a magneto-capillary valve.

In a further embodiment of the present invention step (ii) of the method of the invention is performed in ≤500 µl, ≤400 µl, ≤300 µl, ≤200 µl, ≤100 µl, ≤50 µl or ≤20 µl and step (iii) is performed in ≤50 µl, ≤40 µl, ≤30 µl, ≤20 µl, ≤15 µl, ≤10 µl or ≤5 µl, wherein the buffer solution used in steps (ii) and (iii) has a pH of ≥7.5 or ≥9, with a magneto-capillary valve.

In a preferred embodiment of the present invention step (ii) of the method of the invention is performed in ≤20 µl and step (iii) is performed in ≤5 µl, wherein the buffer solution used in steps (ii) and (iii) has a salt concentration of ≤100 mM, preferably ≤50 mM, more preferably ≤30 mM, most preferably ≤10 mM and a pH of ≥7.5 or ≥9, with a magneto-capillary valve.

In a preferred embodiment of the present invention step (ii) of the method of the invention is performed in ≤20 µl and step (iii) is performed in ≤5 µl wherein the buffer solution used in steps (ii) and (iii) has a salt concentration of ≤100 mM, preferably ≤50 mM, more preferably ≤30 mM, most preferably ≤10 mM and a pH of ≥7.5 or ≥9, with a magneto-capillary valve.

In a further preferred embodiment of the present invention step (ii) of the method of the invention is performed in ≤20 µl and step (iii) is performed in ≤5 µl, wherein the buffer solution used in steps (ii) and (iii) has a salt concentration of ≤30 mM and a pH of ≥7.5, with a magneto-capillary valve.

In another preferred embodiment of the present invention step (ii) of the method of the invention is performed in ≤20 µl and step (iii) is performed in ≤5 µl, wherein the buffer solution used in steps (ii) and (iii) has a salt concentration of ≤30 mM and a pH of ≥9, with a magneto-capillary valve.

In a most preferred embodiment of the present invention step (ii) of the method of the invention is performed in ≤20 µl and step (iii) is performed in ≤5 µl, wherein the buffer solution used in steps (ii) and (iii) has a salt concentration of ≤10 mM and a pH of ≥7.5, with a magneto-capillary valve.

In another most preferred embodiment of the present invention step (ii) of the method of the invention is performed in ≤20 µl and step (iii) is performed in ≤5 µl, wherein the buffer solution used in steps (ii) and (iii) has a salt concentration of ≤10 mM and a pH of ≥9, with a magneto-capillary valve.

In an utmost preferred embodiment of the present invention step (ii) of the method of the invention is performed in ≤20 µl and step (iii) is performed in ≤5 µl, wherein the buffer solution used in steps (ii) and (iii) has a salt concentration of 10 mM and a pH of 9, with a magneto-capillary valve.

In a preferred embodiment of the present invention step (ii) of the method of the invention is performed in ≤20 µl and step (iii) of the method of the invention is performed in ≤5 µl wherein the buffer solution used in steps (ii) and (iii) has a Tris-HCl concentration of ≤100 mM, preferably ≤50 mM, more preferably ≤30 mM, most preferably ≤10 mM and a pH of ≥7.5 or ≥9, with a magneto-capillary valve.

In a further preferred embodiment of the present invention step (ii) of the method of the invention is performed in ≤20 µl and step (iii) is performed in ≤5 µl, wherein the buffer solution used in steps (ii) and (iii) has a Tris-HCl concentration of ≤30 mM and a pH of ≥7.5, with a magneto-capillary valve.

In another preferred embodiment of the present invention step (ii) of the method of the invention is performed in ≤20 µl and step (iii) is performed in ≤5 µl, wherein the buffer solution used in steps (ii) and (iii) has a Tris-HCl concentration of ≤30 mM and a pH of ≥9, with a magneto-capillary valve.

In a most preferred embodiment of the present invention step (ii) of the method of the invention is performed in ≤20 µl and step (iii) is performed in ≤5 µl, wherein the buffer solution used in steps (ii) and (iii) has a Tris-HCl concentration of ≤10 mM and a pH of ≥7.5, with a magneto-capillary valve.

In another most preferred embodiment of the present invention step (ii) of the method of the invention is performed in ≤20 µl and step (iii) is performed in ≤5 µl, wherein the buffer solution used in steps (ii) and (iii) has a Tris-HCl concentration of ≤10 mM and a pH of ≥9, with a magneto-capillary valve.

In an utmost preferred embodiment of the invention step (ii) of the method of the invention is performed in ≤20 µl and step (iii) is performed in ≤5 µl, wherein the buffer solution used in steps (ii) and (iii) has a Tris-HCl concentration of 10 mM and a pH of 9, with a magneto-capillary valve.

According to one embodiment of the present invention, the method of the invention comprises a lysis step prior to step (i) of the method of the invention in any of the above embodiments.

According to one embodiment of the present invention, bound nucleic acids are washed at least twice, preferably twice in step (ii) of the method of the invention in any of the immediate above embodiments of the invention.

In a further embodiment of the present invention nucleic acids are bound to silica coated magnetic particles, step (ii) of the method of the invention is performed in ≤500 μl, ≤400 μl, ≤300 μl, ≤200 μl, ≤100 μl, ≤50 μl or ≤20 μl and step (iii) of the method of the invention is performed in ≤50 μl, ≤40 μl, ≤30 μl, ≤20 μl, ≤15 μl, ≤10 μl or ≤5 μl of buffer solution with a magneto-capillary valve.

In another embodiment of the present invention nucleic acids are bound to silica coated magnetic particles, step (ii) of the method of the invention is performed in ≤500 μl, ≤400 μl, ≤300 μl, ≤200 μl, ≤100 μl, ≤50 μl or ≤20 μl and step (iii) is performed in ≤50 μl, ≤40 μl, ≤30 μl, ≤20 μl, ≤15 μl, ≤10 μl or ≤5 μl, wherein the buffer solution used in steps (ii) and (iii) has a salt concentration of ≤100 mM, preferably ≤50 mM, more preferably ≤30 mM, most preferably ≤10 mM, with a magneto-capillary valve.

In a further embodiment of the present invention nucleic acids are bound to silica coated magnetic particles, step (ii) of the method of the invention is performed in ≤500 μl, ≤400 μl, ≤300 μl, ≤200 μl, ≤100 μl, ≤50 μl or ≤20 μl and step (iii) is performed in ≤50 μl, ≤40 μl, ≤30 μl, ≤20 μl, ≤15 μl, ≤10 μl or ≤5 μl, wherein the buffer solution used in steps (ii) and (iii) has a pH of ≥7.5 or ≥9, with a magneto-capillary valve.

In a preferred embodiment of the present invention nucleic acids are bound to silica coated magnetic particles, step (ii) of the method of the invention is performed in ≤20 μl and step (iii) is performed in ≤5 μl, wherein the buffer solution used in steps (ii) and (iii) has a salt concentration of ≤100 mM, preferably ≤50 mM, more preferably ≤30 mM, most preferably ≤10 mM and a pH of ≥7.5 or ≥9, with a magneto-capillary valve.

In a further preferred embodiment of the present invention nucleic acids are bound to silica coated magnetic particles, step (ii) of the method of the invention is performed in ≤20 μl and step (iii) is performed in ≤5 μl, wherein the buffer solution used in steps (ii) and (iii) has a salt concentration of ≤30 mM and a pH of ≥7.5, with a magneto-capillary valve.

In another preferred embodiment of the present invention nucleic acids are bound to silica coated magnetic particles, step (ii) of the method of the invention is performed in ≤20 μl and step (iii) sis performed in ≤5 μl, wherein the buffer solution used in steps (ii) and (iii) has a salt concentration of ≤30 mM and a pH of ≥9, with a magneto-capillary valve.

In a most preferred embodiment of the present invention nucleic acids are bound to silica coated magnetic particles, step (ii) of the method of the invention is performed in ≤20 μl and step (iii) is performed in ≤5 μl, wherein the buffer solution used in steps (ii) and (iii) has a salt concentration of ≤10 mM and a pH of ≥7.5, with a magneto-capillary valve.

In another most preferred embodiment of the present invention nucleic acids are bound to silica coated magnetic particles, step (ii) of the method of the invention is performed in ≤20 μl and step (iii) is performed in ≤5 μl, wherein the buffer solution used in steps (ii) and (iii) has a salt concentration of ≤10 mM and a pH of ≥9, with a magneto-capillary valve.

In an utmost preferred embodiment of the present invention are bound to silica coated magnetic particles, step (ii) of the method of the invention is performed in ≤20 μl and step (iii) is performed in ≤5 μl, wherein the buffer solution used in steps (ii) and (iii) has a salt concentration of 10 mM and a pH of 9, with a magneto-capillary valve.

In a further preferred embodiment of the present invention nucleic acids are bound to silica coated magnetic particles, step (ii) of the method of the invention is performed in ≤20 μl and step (iii) is performed in ≤5 μl, wherein the buffer solution used in steps (ii) and (iii) has a Tris-HCl concentration of ≤30 mM and a pH of ≥7.5, with a magneto-capillary valve.

In another preferred embodiment of the present invention nucleic acids are bound to silica coated magnetic particles, step (ii) of the method of the invention is performed in ≤20 μl and step (iii) is performed in ≤5 μl, wherein the buffer solution used in steps (ii) and (iii) has a Tris-HCl concentration of ≤30 mM and a pH of ≥9, with a magneto-capillary valve.

In a most preferred embodiment of the present invention nucleic acids are bound to silica coated magnetic particles, step (ii) of the method of the invention is performed in ≤20 μl and step (iii) is performed in ≤5 μl, wherein the buffer solution used in steps (ii) and (iii) has a Tris-HCl concentration of ≤10 mM and a pH of ≥7.5, with a magneto-capillary valve.

In another most preferred embodiment of the present invention nucleic acids are bound to silica coated magnetic particles, step (ii) of the method of the invention is performed in ≤20 μl and step (iii) is performed in ≤5 μl, wherein the buffer solution used in steps (ii) and (iii) has a Tris-HCl concentration of ≤10 mM and a pH of ≥9, with a magneto-capillary valve.

In an utmost preferred embodiment of the present invention are bound to silica coated magnetic particles, step (ii) of the method of the invention is performed in ≤20 μl and step (iii) is performed in ≤5 μl, wherein the buffer solution used in steps (ii) and (iii) has a Tris-HCl concentration of 10 mM and a pH of 9, with a magneto-capillary valve.

According to one embodiment of the present invention, the method of the invention comprises a lysis step prior to step (i) of the method of the invention in any of the immediate above embodiments.

According to one embodiment of the present invention, bound nucleic acids are washed at least twice, preferably twice in step (ii) of the method of the invention in any of the immediate above embodiments of the invention.

According to one embodiment of the present invention, steps (i) to (iii) of the method of the invention are performed at room temperature.

According to another embodiment of the present invention steps (i) and (ii) of the method of the invention are performed at room temperature and step (iii) is performed at a temperature of ≥40° Celsius.

In a preferred embodiment steps (i) and (ii) of the method of the invention are performed at room temperature and step (iii) is performed at a temperature of 50° to 70° Celsius.

In a more preferred embodiment steps (i) and (ii) of the method of the invention are performed at room temperature and step (iii) is performed at 60° to 70° Celsius.

In a most preferred embodiment steps (i) and (ii) of the method of the invention are performed at room temperature and step (iii) of the method of the invention is performed at 65° Celsius.

A further embodiment of the present invention provides for an additional step of detecting the nucleic acids purified using the method of the invention. Detection of purified nucleic acids as used herein comprises enzymatic restriction analysis of purified nucleic acids, amplification, e.g. via PCR such as quantitative real time PCR, nested PCR and other amplification variants known to the person skilled in the art, reverse transcription, hybridization e.g. Southern, Northern blot, microarray analysis or sequencing e.g pyrosequencing, Illumina or Solexa sequencing, SOLiD technology (Applied Biosystems), Heliscope technology (Helicos) or FTIR (Magnotech).

Another aspect of the present invention relates to the use of a buffer solution for purifying nucleic acids, wherein the buffer solution comprising a buffering agent has a salt concentration of ≤500 mM, ≤400 mM, ≤300 mM, ≤200 mM, ≤100 mM, ≤75 mM, ≤50 mM, ≤40 mM, ≤30 mM, ≤20 mM, ≤10 mM, ≤7.5 mM, ≤5 mM, ≤2.5 mM and a pH of ≥7.5, ≥8, ≥8.5, ≥9, ≥9.5 or ≥10.

In one embodiment of the present invention the used buffer solution has a salt concentration of ≤100 mM, preferably ≤50 mM, more preferably ≤30 mM, most preferably ≤10 mM and a pH of ≥7.5, ≥8, ≥8.5, ≥9, ≥9.5 or ≥10.

In a preferred embodiment of the present invention the used buffer solution has a salt concentration of ≤10 mM and a pH of ≥9.

In a more preferred embodiment of the present invention the used buffer solution has a salt concentration of 10 mM and a pH of 9.

In a further embodiment of the present invention the above described buffer solutions are used for washing and eluting nucleic acids.

In another embodiment of the present invention the buffering agent in the above described buffer solutions is Tris-HCl.

In a preferred embodiment of the present invention the used Tris-HCl buffer solution has a salt concentration of ≤10 mM and a pH of ≥9.

In a more preferred embodiment of the present invention the used Tris-HCl buffer solution has a salt concentration of 10 mM and a pH of 9.

In a further embodiment of the present invention the nucleic acids purified with the above described buffer solutions are DNA or RNA.

In another embodiment of the present invention the nucleic acids are bacterial DNA or bacterial RNA.

In a preferred embodiment of the present invention the purified nucleic acids are viral DNA or viral RNA.

A further aspect of the present invention relates to a kit for purifying nucleic acids comprising:
a nucleic acid binding phase,
a buffer solution for washing and eluting of the nucleic acids or a dry form of said buffer solution comprising a buffering agent,
a means for detecting the purified nucleic acids.

The buffer solution of the kit is preferably a buffer solution of the present invention as described in the foregoing embodiments of the invention.

Detection of purified nucleic acids as used herein comprises enzymatic restriction analysis of purified nucleic acids, amplification, e.g. via PCR such as quantitative real time PCR, nested PCR and other amplification variants known to the person skilled in the art, reverse transcription, hybridization e.g. Southern, Northern blot, microarray analysis and sequencing e.g. by pyrosequencing, Illumina or Solexa sequencing, SOLiD technology (Applied Biosystems), Heliscope technology (Helicos) or FTIR (Magnotech).

In another embodiment of the present invention the kit further comprises a miniaturized environment as defined above.

In a further embodiment of the present invention the miniaturized environment contains—a nucleic acid binding phase,
a buffer solution for washing and eluting of the nucleic acids or a dry form of said buffer solution comprising a buffering agent,
a means for detecting the purified nucleic acids.

In another embodiment of the present invention the miniaturized environment is comprised in a cartridge.

In a preferred embodiment of the present invention the kit further comprises a microfluidic device.

In another embodiment of the present invention the kit comprises a cartridge.

In a more preferred embodiment of the present invention the kit comprises a magneto-capillary valve cartridge.

In a further embodiment of the present invention the kit may further comprise a lysing reagent such as chaotropic or kosmotropic salts, detergents, e.g. Triton X, NP40, Tween or SDS, or enzymes such as lysozyme, proteinase K or subtilisin.

In another embodiment of the present invention the kit further comprises a lysing reagent which is not a chaotropic salt or a detergent.

In still another embodiment of the present invention the kit further comprises a lysing reagent which is ammonium sulfate or lithium chloride.

In a further embodiment of the present invention the kit of the invention may include instructions for carrying out nucleic acid purification using the components of the kit.

One embodiment provides the kit of the invention with the components of the kit separately packaged, or stored in separate compartments of a container in which the kit is provided.

Another embodiment of the present invention provides the kit of the invention for use as a diagnostic test. Diagnostic tests may comprise tests to detect diseases caused by or associated with pathogens e.g. bacteria, yeast or viruses or genetic tests, e.g. for genetic disorders, prenatal testing or paternity testing.

In a preferred embodiment of the present invention the kit of the invention is used as a handheld, integrated test for molecular diagnostics. A handheld test for molecular diagnostics may be a small disposable kit or instrument, which is portable and suitable for near patient testing.

EXAMPLES

The methods of the invention for purifying nucleic acids are supported and illustrated by reference to the following examples. It has to be emphasized that these examples should by no means be construed as limiting the scope of the invention.

Example 1: Comparison of Nucleic Acid Yield after Purification by Reference or Single Buffer Solution Methods with Magneto-Capillary Valves (MCV)

In vitro RNA was purified either by a reference method or by the single buffer solution method of the present invention in order to compare nucleic acid/RNA yields. The following protocols were used for the reference method or single buffer solution method, respectively (for an overview see table 1).

TABLE 1

| Protocol steps | Reference method in MCV | Single buffer solution method in MCV |
| --- | --- | --- |
| Lysis | 995 µl 3.3M lysis buffer | 995 µl 3.3M lysis buffer |
| 1rst wash | 20 µl wash buffer 2 (MES hydrate pH 4) | 20 µl 10 mM Tris-HCl, pH 9 |
| 2nd wash | 20 µl wash buffer 2 (MES hydrate pH 4) | 20 µl 10 mM Tris-HCl, pH 9 |
| 3rd wash | 20 µl wash buffer 3 (10 mM Tris-HCl, pH 7) | 20 µl 10 mM Tris-HCl, pH 9 |
| Elution | 3.5 µl elution buffer (10 mM Tris-HCl, pH 7) | 3.5 µl 10 mM Tris-HCl, pH 9 |

Reference Method in MCV

5 µl in vitro RNA was added to 995 µl lysis buffer containing 3.3M guanidinium isothiocyanate (GITC), Tris-HCl, Triton-X100 and EDTA in a 2 ml Eppendorf tube. The sample was mixed on a vortex for 10 seconds for lysis. 20 µl NucliSENS® were added to the sample followed by a mixing step, inverting the Eppendorf tube once upwards and downwards and incubated at room temperature for 3 to 5 minutes to bind the nucleic acids to the magnetic beads.

Figure 1:
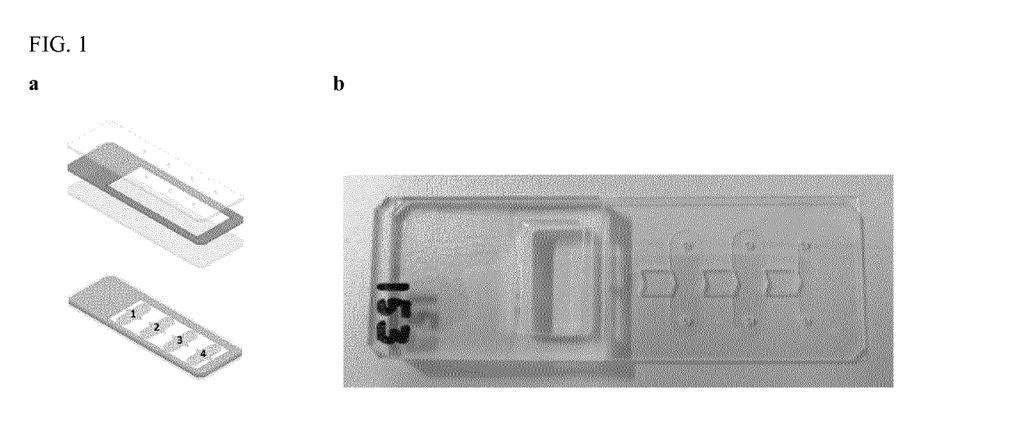
FIG. 1 Magneto-capillary valve cartridge Left: Scheme of a magneto-capillary valve cartridge as exploded (top) and assembled view (bottom), the numbers 1-4 depict different chambers; Right: Assembled cartridge.

After incubation of the sample with the lysis buffer and the magnetic beads, the sample was pipetted into a Magneto capillary valve (MCV) cartridge as described in den Dulk et al., 2013 and as shown in FIG. 1. The MCV cartridge contains a first washing chamber 1, a second washing chamber 2, and a third washing chamber 3. The first washing chamber 1 and the second washing chamber 2 of the MCV cartridge were each prefilled with 20 µl of wash buffer 2. The third washing chamber 3 was filled with 20 µl wash buffer 3. The MCV cartridge contains an elution chamber 4. The elution chamber 4 was filled with 3.5 µl of elution buffer containing a low salt concentration of 10 mM Tris-HCl.

Magnetic beads were collected and moved using a magnet as described by den Dulk et al., 2013. First, the NucliSENS® beads were collected in the concentrator part where the sample was located. A magnet then transfers the magnetic beads through the valve to the first wash chamber 1. In that chamber the magnetic beads were washed using the magnet. This process was repeated in the second wash chamber 2 and the third wash chamber 3. In the elution chamber 4, the nucleic acids were eluted from the beads by increasing the temperature to 65°. for 2 minutes and subsequent mixing using the magnet.

Single Buffer Method in MCV

The method was similar to the 'Reference method in MCV' as described above. The only difference was the composition of the buffers which was the same for both washing steps and the final elution step (10 mM Tris-HCl at a pH of 9)

Figure 2:
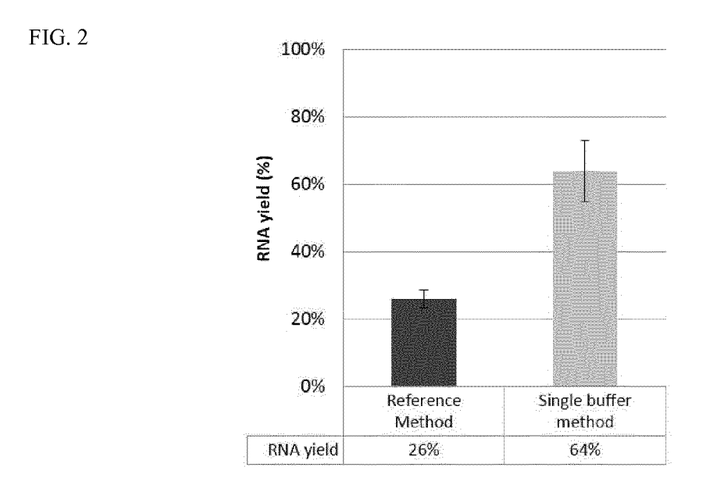
FIG. 2 ivRNA yield comparison using MCV Black column: RNA yield obtained by reference method; Grey column: RNA yield obtained by the single buffer solution method.

As can be derived from FIG. 2, the RNA yield obtained by the single buffer solution
method using a MCV is significantly higher than the yield obtained by the reference method, with an average RNA yield of 64% of the RNA, initially bound to the magnetic beads obtained by the single buffer solution method versus 26% of the RNA, initially bound to the magnetic beads, obtained by the reference method.

Example 2: Comparison of Nucleic Acid Yield after Purification by Reference or Single Buffer Solution Methods with Eppendorf Tubes In vitro RNA was purified either by a reference method or by the single buffer solution method of the present invention in order to compare nucleic acid/RNA yields. The following protocols were used for the reference method or single buffer solution method, respectively (for an overview see table 2).

TABLE 2

| Protocol steps | Reference method | Single buffer solution method |
| --- | --- | --- |
| Lysis | 995 µl 3.3M lysis buffer | 995 µl 3.3M lysis buffer |
| 1rst wash | 50 µl wash buffer 2 (MES hydrate pH 4) | 50 µl 10 mM Tris-HCl, pH 9 |
| 2nd wash | 50 µl wash buffer 3 buffer (10 mM Tris-HCl, pH 7) | 50 µl 10 mM Tris-HCl, pH 9 |
| Elution | 50 µl elution buffer buffer (10 mM Tris-HCl, pH 7) | 50 µl elution buffer (10 mM Tris-HCl, pH 9) |

Reference Method:

5 µl in vitro RNA was added to 995 µl lysis buffer containing 3.3M guanidinium isothiocyanate (GITC), Tris-HCl, Triton-X100 and EDTA in a 2 ml Eppendorf tube. The sample was mixed on a vortex for 10 seconds for lysis. 20 µl NucliSENS® beads or 8 µl MagPrep® Silica particles (same final concentration) were added to the sample followed by a mixing step, inverting the eppendorf tube once upwards and downwards and incubated at room temperature for 3 to 5 minutes to bind the nucleic acids to the beads or particles, respectively.

After incubation of the sample with the lysis buffer and the magnetic beads or particles, the tube was placed on a magnetic rack to pull the beads or particles with the bound nucleic acids to the side of the tube. By removing the liquid using a pipette, impurities such as debris and proteins were removed.

Subsequently, the magnetic particles were washed at room temperature with 50 µl wash buffer 2, containing MES hydrate salt pH 4 to dilute/replace the amount of GITC, while keeping the nucleic acids bound to the magnetic beads or particles. In every wash step wash liquid was added to the tube, the magnetic beads or particles were subsequently mixed with the liquid, the tube was placed on the magnetic rack to pull the beads or particles with the bound nucleic acids to the side of the tube and finally the liquid was removed.

The second wash step was performed at room temperature using 50 µl washing buffer 3, containing Tris-HCl at pH 7 to dilute/replace the amount of MES hydrate salt and increase the pH for better elution.

Finally, 50 µl elution buffer solution containing Tris-HCl pH 7 was added, incubated with the magnetic beads or particles for 5 minutes at 65° Celsius on an Eppendorf thermo heater and subsequently vortexed for 10 seconds to elute the nucleic acids from the magnetic beads or particles.

Single Buffer Solution Method:

5 µl in vitro RNA was added to 995 µl lysis buffer containing 3.3M guanidinium isothiocyanate (GITC), Tris-HCl, Triton-X100 and EDTA in a 2 ml Eppendorf tube. The sample was mixed on a vortex for 10 seconds for lysis. 20 µl NucliSENS® beads or 8 µl MagPrep® Silica particles (same final concentration) were added to the sample followed by a mixing step, inverting the eppendorf tube once upwards and downwards and incubated at room temperature for 3 to 5 minutes to bind the nucleic acids to the beads or particles, respectively.

After incubation of the sample with the lysis buffer and the magnetic beads or particles, the tube was placed on a magnetic rack to pull the beads or particles with the bound nucleic acids to the side of the tube. By removing the liquid using a pipette, impurities such as debris and proteins were removed.

Subsequently, the magnetic particles were washed twice at room temperature with 50 µl buffer solution containing Tris-HCl pH 9 to dilute/replace the amount of GITC and increase the pH for subsequent elution, while still keeping the nucleic acids bound to the magnetic beads or particles. In every wash step wash liquid was added to the tube, the magnetic beads or particles were subsequently mixed with the liquid, the tube was placed on the magnetic rack to pull the beads or particles with the bound nucleic acids to the side of the tube and the liquid was removed.

Finally, 50 µl buffer solution containing Tris-HCl pH 9 was added, incubated with the magnetic beads or particles for 5 minutes at 65° Celsius on an Eppendorf thermo heater and subsequently vortexed for 10 seconds to elute the nucleic acids from the magnetic beads or particles.

Figure 3:
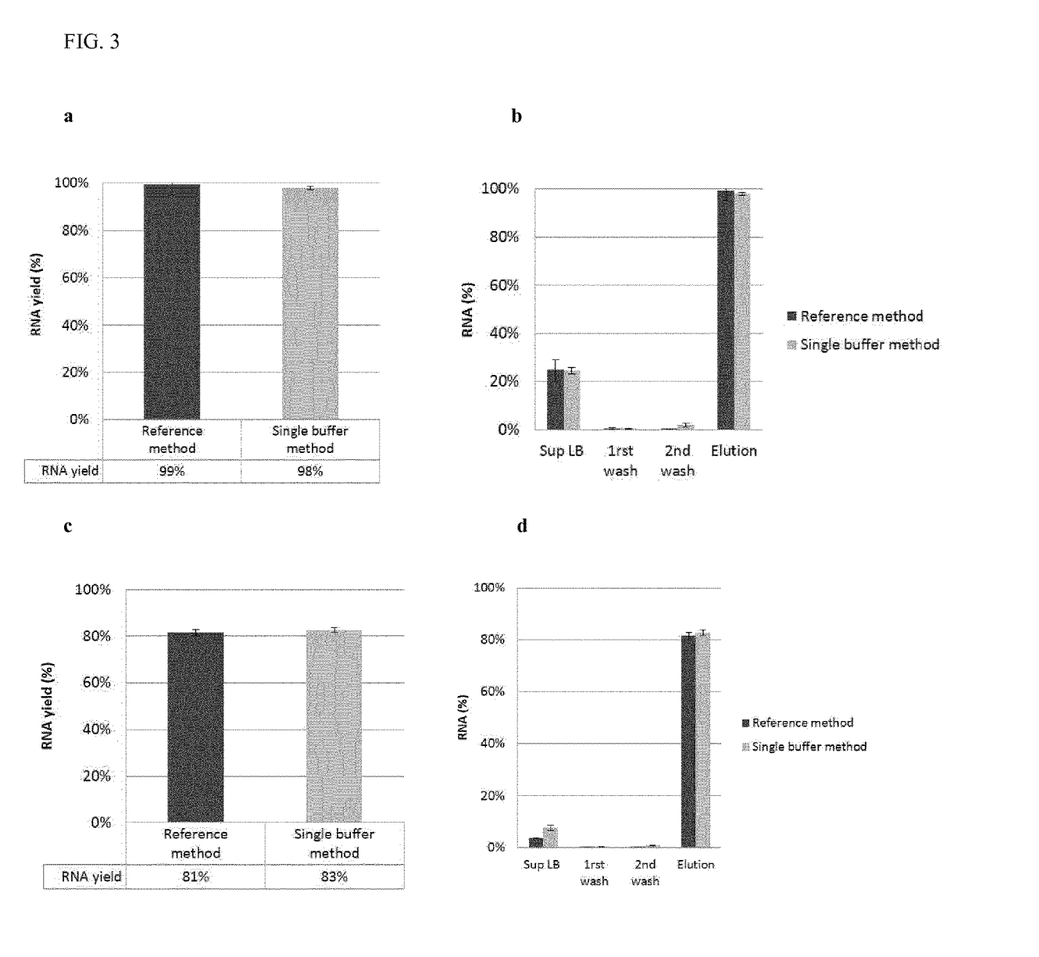
FIG. 3 ivRNA yield comparison using Eppendorf tubes (a) Black column: RNA yield obtained by reference method using NucliSENS® beads; Grey column: RNA yield obtained by the single buffer solution method using NucliSENS® beads; (b) Percentage RNA detected in different fractions, indicated on the x axis when using NucliSENS® beads with the reference method (black columns) or single buffer method (grey columns); (c) Black column: RNA yield obtained by reference method using MagPrep® Silica particles; Grey column: RNA yield obtained by the single buffer solution method using MagPrep® Silica particles; (d) Percentage RNA detected in different fractions, indicated on the x axis when using MagPrep® Silica particles with the reference method (black columns) or single buffer method (grey columns)

As can be derived from FIG. 3a and FIG. 3c, the RNA yield obtained by the reference (black column) and the single buffer method (grey column) is similar using a wash and elution volume of 50 µl. When using NucliSENS® beads, around 99% of the RNA amount present in the sample before purification was obtained in purified form (FIG. 3a) and when using MagPrep® Silica particles, around 82% of the RNA amount present in the sample before purification was obtained in purified form (FIG. 3c).

In FIGS. 3b and 3d the percentage of RNA amount present in the sample before purification was detected in different fractions (Sup LB, 1rst wash, 2nd wash and elution fraction).

The percentage of RNA that could be detected in the supernatant fraction after lysis and binding to the magnetic beads or particles (Sup LB) was similar using the reference and single buffer solution method using both NucliSENS® beads (FIG. 3b) and MagPrep® Silica Particles (FIG. 3d). Therefore, the percentage amounts of unbound RNA are almost identical for both methods when using different nucleic acid binding phases.

It was also shown that hardly any bound RNA got lost from the NucliSENS® beads or MagPrep® Silica particles during the first and second washing steps using either method (see middle columns of FIG. 3b and FIG. 3d).

As a result, most of the RNA initially bound to the magnetic beads or particles, around 99% for the NucliSENS® beads and around 80% for the MagPrep® Silica particles, was found in the elution fractions (see far right columns of FIG. 3b and FIG. 3d).

In summary, the above results show that while using a single wash and elution buffer, the single buffer solution method in Eppendorf tubes achieves similar nucleic acid yields as reference methods when identical small wash and elution volumes are employed.

LIST OF REFERENCE SIGNS

1. Boom et al., 1990, "Rapid and Simple Method for Purification of Nucleic Acids", Journal of Clinical Microbiology, 28, 495-503
2. EP 0 389 063
3. US 2014/0272999
4. den Dulk et al., 2013, "Magneto-capillary valve for integrated purification and enrichment of nucleic acids and proteins", Lab Chip, 13, 106-118

The invention claimed is:

1. A method for purifying nucleic acids using a single buffer solution, comprising:

exposing a liquid sample to a nucleic acid binding phase, wherein the liquid sample comprises nucleic acids, wherein the nucleic acid binding phase comprises magnetic particles, silica particles, or a mixture thereof; and
   allowing the nucleic acids to bind to the nucleic acid binding phase,
   removing a liquid phase containing an impurity from the nucleic acid binding phase,
   washing the nucleic acids bound to the nucleic acid binding phase at least once with the single buffer solution,
      wherein the buffer solution comprises a buffering agent, and
      wherein the washing is carried out at room temperature; and
   eluting the nucleic acids from the nucleic acid binding phase with ≤50 µl of the single buffer solution, wherein eluting the nucleic acids is performed at a temperature of ≥40° Celsius.

2. The method according to claim 1, wherein the single buffer solution has a salt concentration ≤100 mM.

3. The method according to claim 1, wherein the single buffer solution has a pH of ≥7.5.

4. The method according to claim 1, wherein the buffering agent in the single buffer solution is Tris-HCl.

5. The method according to claim 4, wherein washing the nucleic acids is performed in ≤200 µl of the single buffer solution.

6. The method according to claim 5, wherein eluting the nucleic acids is performed in ≤15 µl of the single buffer solution.

7. The method according to claim 1, wherein the sample comprises lysed cells.

8. The method according to claim 1, wherein the nucleic acid binding phase comprises silica particles.

9. The method according to claim 8, wherein the nucleic acid binding phase comprises magnetic particles.

10. The method according to claim 9, wherein the method is performed with a microfluidic device.

11. The method according to claim 10, wherein the method is performed with a magneto-capillary valve.

12. The method according to claim 1,
   wherein exposing the sample, allowing the nucleic acids to bind to the nucleic acid binding phase, and washing the nucleic acids are carried out at room temperature, and
   wherein eluting the nucleic acids from the nucleic acid binding phase is performed at a temperature of 50° to 70° Celsius.

13. The method according to claim 1, wherein the buffer solution of has a salt concentration of ≤10 mM.

14. The method according to claim 1, wherein the buffer solution has a pH of ≥9.

15. The method according to claim 4, wherein washing the nucleic acids is performed in ≤20 µl of the single buffer solution.

16. The method according to claim 5, wherein eluting the nucleic acids is performed in ≤5 µl of the single buffer solution.

17. The method according to claim 12,
   wherein eluting the nucleic acids from the nucleic acid binding phase is performed at a temperature of 65° Celsius.

* * * * *